(12) United States Patent
Zhang et al.

(10) Patent No.: US 10,799,210 B1
(45) Date of Patent: Oct. 13, 2020

(54) DENTAL IMAGING APPARATUS AND METHOD

(71) Applicant: S-Ray Incorporated, Portland, OR (US)

(72) Inventors: Jimin Zhang, Bellevue, WA (US); Scott Parker, Woodinville, WA (US); Don Brocha, Woodinville, WA (US); Bryce Greenhalgh, Woodinville, WA (US); Steve Baird, Bainbridge Island, WA (US)

(73) Assignee: S-Ray Incorporated, Portland, OR (US)

( * ) Notice: Subject to any disclaimer, the term of this patent is extended or adjusted under 35 U.S.C. 154(b) by 220 days.

(21) Appl. No.: 16/116,497

(22) Filed: Aug. 29, 2018

Related U.S. Application Data

(60) Provisional application No. 62/553,629, filed on Sep. 1, 2017.

(51) Int. Cl.
| | |
|---|---|
| *A61B 5/00* | (2006.01) |
| *A61B 8/00* | (2006.01) |
| *A61B 8/12* | (2006.01) |
| *A61B 1/24* | (2006.01) |
| *A61C 9/00* | (2006.01) |
| *A61B 8/08* | (2006.01) |

(52) U.S. Cl.
CPC .............. *A61B 8/4416* (2013.01); *A61B 1/24* (2013.01); *A61B 8/12* (2013.01); *A61B 8/4488* (2013.01); *A61B 8/483* (2013.01); *A61B 8/5261* (2013.01); *A61C 9/0053* (2013.01); *A61C 9/0086* (2013.01)

(58) Field of Classification Search
CPC .................................. A61K 6/00; A61K 8/00
USPC ......................................................... 382/128
See application file for complete search history.

(56) References Cited

U.S. PATENT DOCUMENTS

| | | | |
|---|---|---|---|
| 5,100,318 A * | 3/1992 | Demyun | A61C 19/043 |
| | | | 433/215 |
| 5,115,813 A | 5/1992 | Ylander et al. | |
| 5,755,571 A | 5/1998 | Companion | |
| 6,050,821 A | 4/2000 | Klaassen et al. | |
| 6,589,054 B2 | 7/2003 | Tingley et al. | |
| 6,620,101 B2 | 9/2003 | Azzam et al. | |
| 6,638,219 B1 | 10/2003 | Asch et al. | |
| 6,702,746 B1 | 3/2004 | Samer | |
| 6,997,883 B1 | 2/2006 | Hahn | |
| 7,004,903 B2 | 2/2006 | Cadossi et al. | |
| 7,285,093 B2 | 10/2007 | Anisimov et al. | |
| 8,926,518 B2 | 1/2015 | Culjat et al. | |
| 2002/0100326 A1 | 8/2002 | Stein | |
| 2003/0023167 A1 | 1/2003 | Azzam et al. | |
| 2003/0195423 A1 | 10/2003 | Gibbs et al. | |

(Continued)

FOREIGN PATENT DOCUMENTS

| | | |
|---|---|---|
| AU | 2002 249542 A1 | 7/2002 |
| DE | 3620404 A1 | 1/1988 |

(Continued)

*Primary Examiner* — Abolfazl Tabatabai
(74) *Attorney, Agent, or Firm* — Klarquist Sparkman, LLP

(57) ABSTRACT

In one representative embodiment, an intraoral scanning device includes a scan head sized and shaped to be placed inside a patient's mouth. The scan head can include at least one ultrasonic transducer for generating ultrasonic images and at least one light-based sensor for generating optical images.

27 Claims, 8 Drawing Sheets

(56) References Cited

U.S. PATENT DOCUMENTS

| | | |
|---|---|---|
| 2004/0019262 A1 | 1/2004 | Perelgut |
| 2005/0070797 A1 | 3/2005 | Cadossi et al. |
| 2005/0196725 A1 | 9/2005 | Fu |
| 2007/0037125 A1 | 2/2007 | Maev et al. |
| 2007/0238996 A1 | 10/2007 | Lin et al. |
| 2009/0099408 A1 | 4/2009 | Abolfathi et al. |
| 2009/0263759 A1 | 10/2009 | Van Herpern |
| 2012/0040312 A1 | 2/2012 | Hinders |
| 2012/0244489 A1 | 9/2012 | Carnahan |
| 2015/0105665 A1 | 4/2015 | Kim et al. |
| 2015/0245896 A1 | 9/2015 | Montgomery |
| 2015/0313572 A1 | 11/2015 | Gerbaulet et al. |
| 2016/0113745 A1 | 4/2016 | Golub et al. |

FOREIGN PATENT DOCUMENTS

| | | |
|---|---|---|
| DE | 4205360 A1 | 8/1993 |
| DE | 103 18 579 A1 | 11/2004 |
| EP | 0353209 A1 | 1/1990 |
| FR | 2627978 A1 | 9/1989 |
| GB | 1102491 | 2/1968 |
| JP | 57196104 A | 12/1982 |
| JP | 57204407 A | 12/1982 |
| JP | 2006-025904 A | 2/2006 |
| JP | 2007-330541 A | 12/2007 |
| RU | 2176491 C2 | 12/2001 |
| WO | WO1987/000028 A1 | 1/1987 |
| WO | WO1989/003195 A1 | 4/1989 |
| WO | WO1995/004506 A1 | 2/1995 |
| WO | WO1999/062423 A1 | 12/1999 |
| WO | WO2002/054948 A1 | 7/2002 |
| WO | WO2002/060333 A1 | 8/2002 |
| WO | WO2002/085178 A2 | 10/2002 |
| WO | WO2003/009772 A1 | 2/2003 |
| WO | WO2003/039389 A1 | 5/2003 |
| WO | WO2003/053247 A1 | 7/2003 |
| WO | WO2005/034785 A2 | 4/2005 |

\* cited by examiner

DENTAL IMAGING APPARATUS AND METHOD

CROSS REFERENCE TO RELATED APPLICATION

This application claims the benefit of U.S. Provisional Patent Application No. 62/553,629, filed Sep. 1, 2017, which is incorporated herein by reference.

FIELD

The present disclosure relates to a dental imaging apparatus that can include hand-held dental scanners that are used in a patient's mouth to examine the teeth and gums.

BACKGROUND

Intraoral scanners are finding more use in the practice of dentistry. Existing scanners typically use light-based systems, such as lasers, light frequencies and cameras to provide images of a patient's teeth and gum tissue.

Currently available existing scanners are limited to a single scan surface on the end of the inspection wand or probe. Additionally, existing wands typically are larger than a conventional tooth brush and therefore are larger than the generally accepted size for patient comfort. The scan surfaces of existing wands are non-adjustable relative to the handle, which may require the operator to force the patient's mouth open to a very wide degree in order to position the scan surface facing the surface of the tooth under inspection. Moreover, existing scanners that use light-based systems cannot provide images or data from subgingival areas (below the gum line), which is necessary to detect problems such as gum disease (e.g., in the perio pocket) and cracks below the gum line (which may require tooth extraction).

SUMMARY

The present disclosure describes various embodiments of dental imaging devices that desirably, although not necessarily, can address one or more of the problems described above.

In some embodiments, a hand-held intraoral scanner has a relatively small scan head and scanning surface compared to existing devices to improve patient comfort and to allow placement at locations within the patient's mouth that a larger scanner cannot reach.

In some embodiments, an intraoral scanner can have two scanning surfaces (e.g., on opposite sides of the scan head) to permit scanning of two surfaces, such as the buccal and lingual surfaces of a tooth or teeth on the upper or lower arch, and desirably is configured to fit comfortably within a patient's mouth to permit such scanning without the patient having to open their mouth wide. In some embodiments, the intraoral scanner can have a third scanning surface to permit scanning of a third surface, such as the occlusal surface, of a tooth or teeth. In some embodiments, the intraoral scanner can permit scanning of three sides of a tooth (e.g., the buccal, lingual and occlusal surfaces).

In some embodiments, an intraoral scanner can have a scan head that is rotatable relative to a handle to facilitate placement of the scanning surface at the desired position within a patient's mouth. The scanner can also be used for other internal, non-dental applications or external applications (outside the patient's body) where limited space and access is available. At any time during a procedure, the user can remove the scanner from the current scanning location, adjust the position of the scan head by rotating it relative to the handle, and reposition the scan head at a different location for a new scan or inspection intraorally or externally.

In some embodiments, an intraoral scanner can include one or more ultrasound transducers that allow the scanning of subgingival areas which can be used, for example, to detect gum disease and cracks that would require extraction of a tooth.

In some embodiments, an intraoral scanner can utilize through transmission ultrasound with a tooth positioned between two transducers, which can be used to map internal aspects of a tooth or teeth and surrounding tissue (e.g., gum tissue) and generate a three-dimensional image of the tooth or teeth and surrounding tissue.

In some embodiments, an intraoral scanner can include one or more light-based image sensors for generating optical images of exposed tissue (the portion of a tooth or teeth above the gums as well as the gums) and ultrasound images of subgingival areas. The sensors can be connected to a controller and a color display that can display in real-time, three-dimensional images of a tooth or teeth and subgingival areas of the patient's mouth.

In some embodiments, an intraoral scanner can include two cameras positioned on opposite sides of an array of ultrasonic transducers, which can be used to produce a three-dimensional image of the surface of a tooth or teeth and the surrounding tissue. The image can be used which can be used, for example, to (i) produce a three-dimensional impression of the intraoral teeth, (ii) obtain a three-dimensional impression faster and more accurate due to the scanning of three surfaces at the same time, (iii) guide the user to observe or monitor the real-time ultrasound of the internal structure of the teeth or surrounding tissues.

In some embodiments, a color display can present simultaneous views of the optical and ultrasound scans. Because both scan systems are integrated, the operator has access to more information as compared to existing optical scanners, which are limited by common issues such as reflective surfaces and very confined interproximal or interdental areas.

In some embodiments, a dental imaging system can utilize optical and ultrasound signal generation in combination with a collection module and video monitor having multiple connection ports to support a variety of optical and ultrasound scan heads or applicators. The collection module can be mounted on a portable stand with battery power. The stand can be positioned in close proximity to or integrated as part of the patient chair.

In some embodiments, the collection module can have multiple connection ports to support a variety of scanning units in various configurations to provide a dentist or dental staff various options for examination of a particular tooth or teeth.

In some embodiments, the collection module can include software that enables conversion of scan data into a variety of file and display options including STL and Point Cloud, which provide real-time, three-dimensional images of the surface contours of teeth, including accurate color detail as well as three-dimensional images from the crown to the root. The images can be used in a Computer Aided Design (CAD) system for manufacturing dental restorations and other implants (e.g., prosthetic teeth) with color matching.

In one embodiment, an intraoral scanning device comprises a scan head sized and shaped to be placed inside a patient's mouth, the scan head comprising at least one ultrasonic transducer for generating ultrasonic images and at least one light-based image sensor for generating optical images.

In some embodiments, the at least one ultrasonic transducer comprises an array of ultrasonic transducers.

In some embodiments, the scan head comprises at least one light source.

In some embodiments, the at least one light source comprises an LED.

In some embodiments, the at least one light-based image sensor comprises a CCD or CMOS sensor.

In some embodiments, the at least one ultrasonic transducer comprises an array of ultrasonic transducers and the at least one light-based image sensor comprises first and second light-based image sensors positioned on opposite sides of the array of ultrasonic transducers.

In some embodiments, the intraoral scanning device further comprises a handle, and the scan head is coupled to one end of the handle.

In some embodiments, the scan head is configured to be pivotable relative to the handle.

In some embodiments, the scan head comprises first and second opposing scan surfaces configured to be placed against or adjacent opposing sides of a tooth.

In some embodiments, the scan head comprises a third scan surface extending between the first and second scan surfaces, the third scan surface configured to be placed against or adjacent an occlusal surface of a tooth.

In another embodiment, an intraoral scanning device comprises a handle and a scan head coupled to a distal end portion of the handle and sized and shaped to be placed inside a patient's mouth. The scan head comprises at least one sensor for generating images of tissue inside the patient's mouth, wherein the scan head is configured to be pivotable relative to the handle about a pivot axis.

In some embodiments, at least one of the handle and the scan head comprises an indexing feature configured to retain the scan head relative to the handle in one of a plurality of different positions relative to the handle.

In some embodiments, the indexing feature comprises a plurality of balls on one of the handle and the scan head and the other of the handle and the scan head comprises at least one detent configured to receive one of the balls as the scan head is pivoted relative to the handle.

In some embodiments, the scan head comprises at least one ultrasonic transducer.

In some embodiments, the scan head comprises at least one light-based image sensor.

In another embodiment, a dental imaging apparatus comprises an intraoral device comprising at least one ultrasonic transducer for generating ultrasonic images and at least one light-based image sensor for generating optical images; and a visual display in communication with the intraoral device, the visual display configured to display ultrasonic images and optical images.

In some embodiments, the intraoral device comprises a handle and a scan head coupled to one end of the handle, wherein the sensors are mounted on the scan head.

In another embodiment, a method comprises inserting an intraoral device inside a patient's mouth, the intraoral device comprising at least one ultrasonic transducer and at least one light-based image sensor; and generating an ultrasound image and an optical image of tissue inside the patient's mouth.

In some embodiments, method further comprises displaying the ultrasound image and the optical image on a visual display.

In some embodiments, the act of displaying comprises simultaneously displaying the ultrasound image and the optical image on the visual display.

In some embodiments, the optical image is an image of a portion of a tooth or teeth above the gum line and the ultrasound image is an image of a portion of the tooth or teeth below the gum line and tissue surrounding the tooth or teeth.

In some embodiments, the method further comprises using the optical image as a guide to evaluate gum tissue of the tooth or teeth.

In some embodiments, the method further comprises storing the optical image and the ultrasound image and evaluating changes to the tooth or teeth and surrounding tissue over time.

In some embodiments, the method further comprises positioning the intraoral device at a particular location inside the patient's mouth while viewing the optical image on a display.

In some embodiments, the act of generating comprises generating a three-dimensional volumetric optical image of a tooth or teeth above the gum line and generating a three-dimensional ultrasonic image of a portion of the tooth or teeth below the gum line and tissue surrounding the tooth or teeth.

In some embodiments, the method further comprises generating a fused image comprising the three-dimensional volumetric optical image and the three-dimensional ultrasonic image.

In another representative embodiment, a dental imaging apparatus comprises an intraoral device comprising at least three scan panels configured to be placed adjacent three surfaces of a tooth or teeth, each scan panel having at least one ultrasonic transducer for generating ultrasonic images and at least one light-based sensor for generating an optical images; and a computing device in communication with the intraoral device configured to generate a three-dimensional impression of intraoral structure in multiple directions simultaneously.

The foregoing and other objects, features, and advantages of the invention will become more apparent from the following detailed description, which proceeds with reference to the accompanying figures.

DETAILED DESCRIPTION

Figure 1:
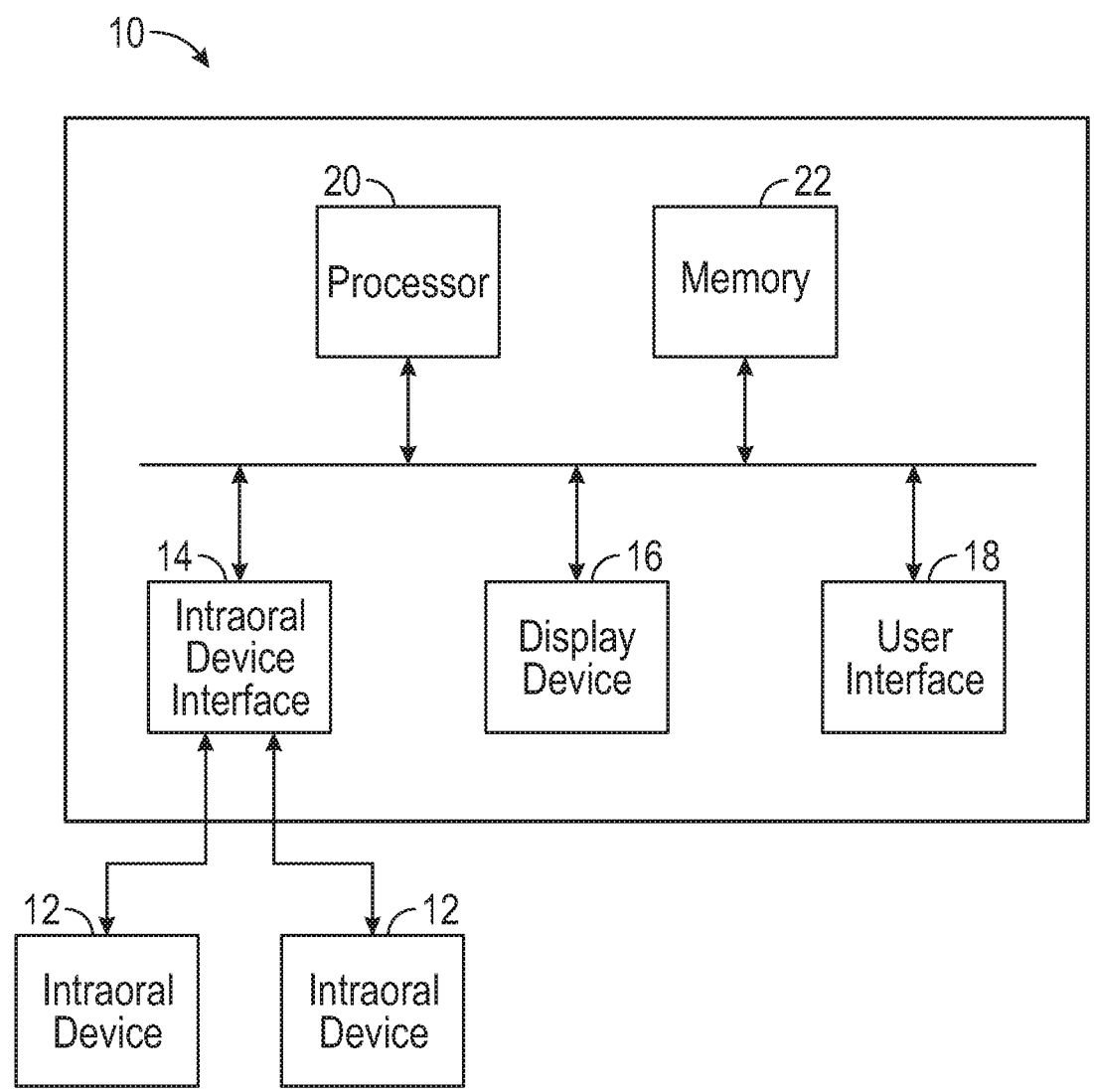
FIG. 1 is a block diagram of a dental imaging apparatus, according to one embodiment.

FIG. 1 is a block diagram of a dental imaging apparatus 10, according to one embodiment. The apparatus 10 can include one or more intraoral devices 12 that are in communication with an intraoral device interface 14. The intraoral devices 12 can take the form of, for example, probes, wands, mouthpieces, and other devices configured to be placed in a patient's mouth in order to obtain images of tissue in the mouth, as further described below. The apparatus 10 can further include a display device 16 (e.g., a computer screen or monitor), a user interface 18 (e.g., a keyboard, computer mouse, touch screen, etc.), a processor 20, and memory 22, all of which are in communication with each other and/or the intraoral device interface 14 via wired or wireless connections. The intraoral devices 12 transmit signals or data representative of images (e.g., ultrasonic images and/or optical images) of tissue inside the patient's mouth to the intraoral device interface 14 for processing by the processor 20. The images can be displayed on the display device 16 and/or stored in memory 22. The user interface 18 can allow a user to control a program stored on memory 22 that is executed by the processor 20.

Figure 2:
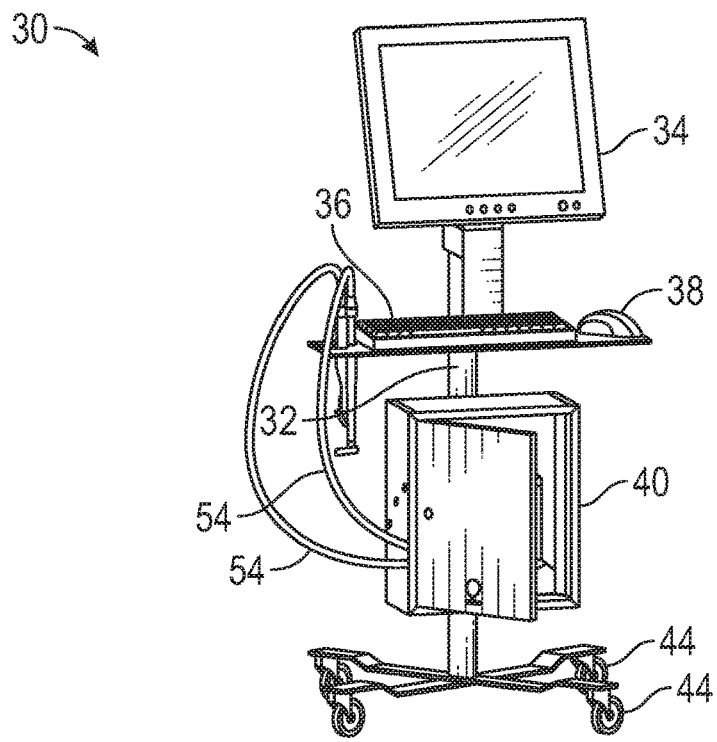
FIGS. 2-4 are perspective view of a dental imaging apparatus, according to another embodiment.
Figure 3:
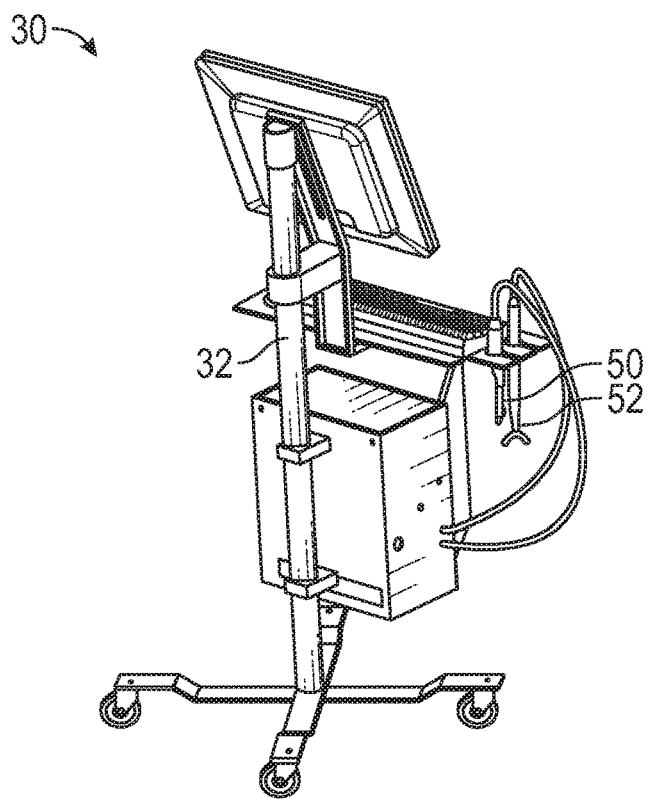
Figure 4:
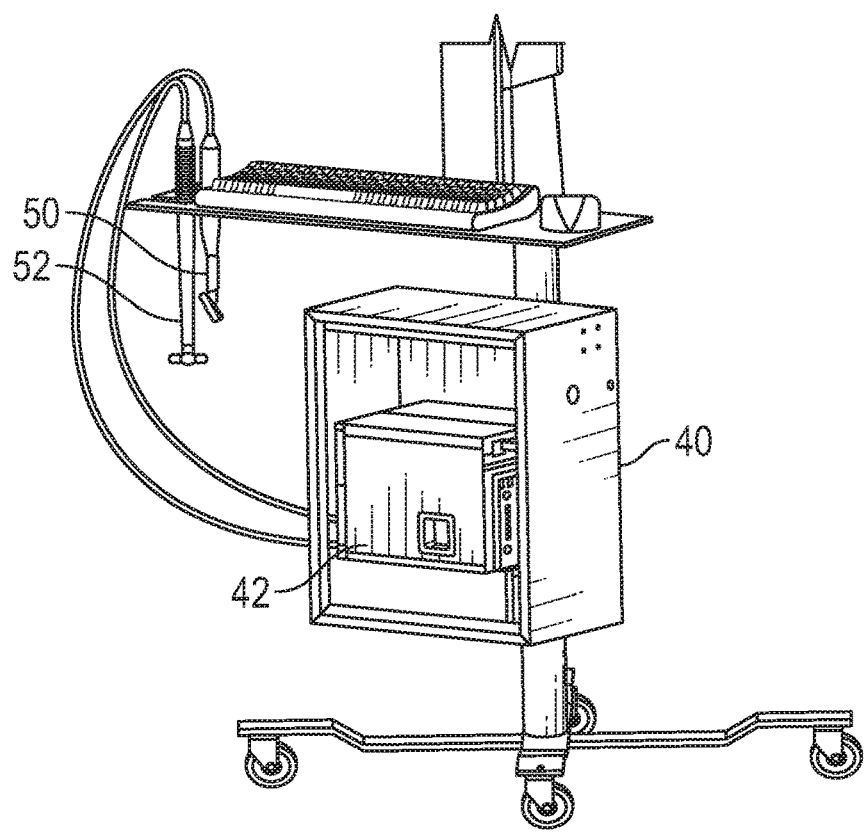

FIGS. 2-4 shows a dental imaging apparatus 30, according to another embodiment. The apparatus 30 is configured to be used in a dental office adjacent or near a patient chair. The apparatus 30 can include a frame 32 on which a visual display 34, a keyboard 36, a computer mouse 38, and a cabinet 40 can be mounted. A computing device or controller 42 (also referred to herein as a collection module) can be housed in the cabinet 40. The frame 32 can be mounted on casters or wheels 44 to enable portability of the apparatus. The computing device 42 can be, for example, a general purpose computer and can be connected to the Internet via a wired or wireless connection (e.g., a WIFI connection), as known in the art. The display 34 can be, for example, a liquid crystal display, a plasma display, another type of display device known in the art.

The apparatus 30 can include a first intraoral wand or probe 50 and a second intraoral wand or probe 52. The probes 50, 52 can be connected to the computing device 42 via respective cables 54. In alternative embodiments, each of the probes 50, 52 can be in communication with the computing device 42 via a wireless connection, such as a Bluetooth connection. Although two probes are shown in the illustrated embodiment, the apparatus can alternatively include a single probe or more than two probes. Further, the apparatus can include other types of intraoral devices, such as mouthpieces or similar types of devices configured to be mounted directly on one or more teeth or other tissue within the patient's mouth.

The computing device 42 can function as an intraoral device interface 14 for receiving signals from the probes 50, 52. The signals from the probes can be processed by an onboard processor of the computing device and/or saved in memory of the computing device 42.

Figure 5:
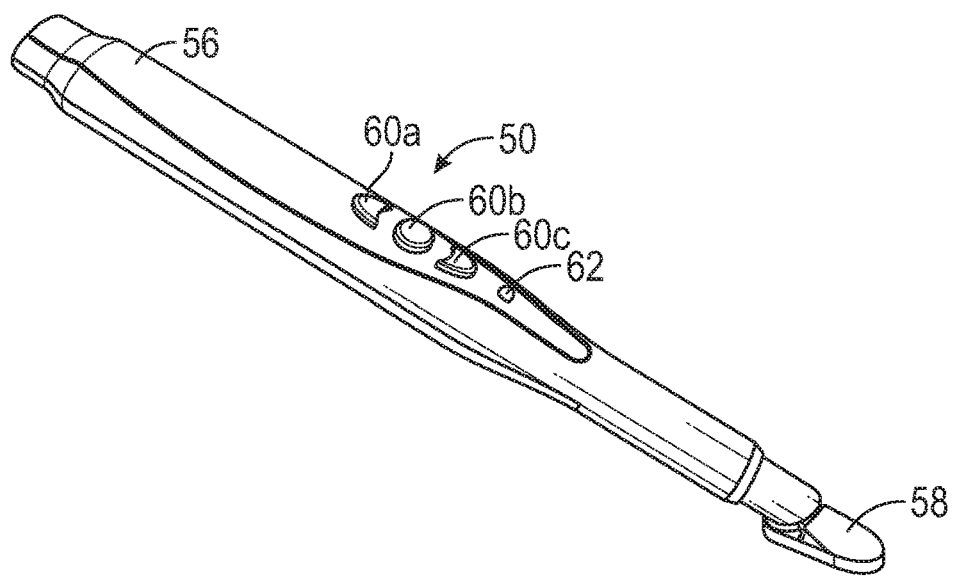
FIG. 5 is a perspective view of one of the intraoral probes of the dental imaging apparatus of FIGS. 2-4.

Referring to FIG. 5, the first probe 50 can include a handle 56 and a scan head 58 coupled to the distal end portion of the handle. The scan head 58 can include one or more light-based image sensors and/or ultrasonic sensors for generating images, as further described below. The handle 56 can include one or more buttons or switches configured to control various functions of the probe, including a button 60a for controlling video capture length (time), a button 60b for controlling optical and ultrasonic scanning, and a button 60c for controlling LED light intensity and pulsing. The handle 56 can also include a power indicator light 62.

Figure 8:
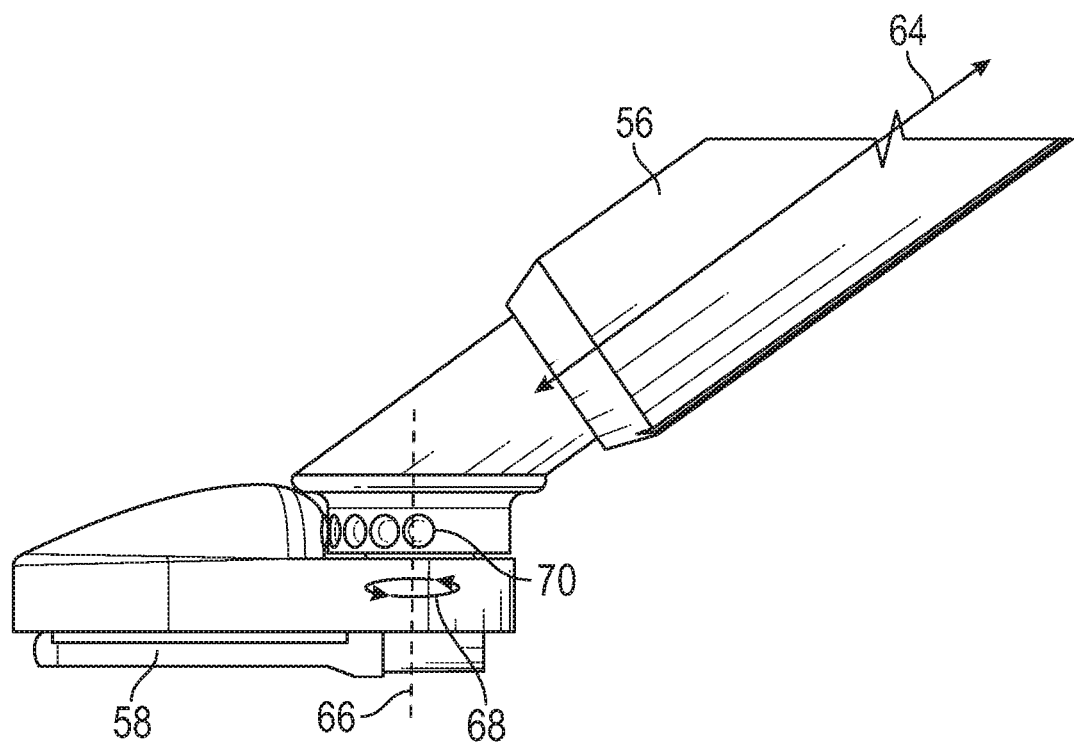
FIG. 8 is a side view of the scan head and the distal end portion of the handle of the probe of FIG. 5.

In particular embodiments, the scan head 58 can be pivotably or rotatably connected to the handle 56 to permit pivoting of the scan head relative to the handle. In this manner, the scan head 58 can be pivoted to multiple positions relative to handle 56 to facilitate placement of the scan head at a desired position within the patient's mouth. As shown in FIG. 8, for example, the scan head 58 in the illustrated embodiment can extend from the handle 56 at about a 45 degree angle relative to the longitudinal axis 64 of the handle and can be connected to the handle to permit pivoting of the scan head about a pivot axis 66. The pivot axis 66 can be oriented at about a 135 degree angle relative to the longitudinal axis 64 of the handle. The scan head 58 can pivot about the pivot axis 66 in two directions (indicated by double-headed arrow 68) in a plane that is perpendicular to the page in FIG. 8. In particular embodiments, the scan head 58 can be pivoted relative to the handle through a range of motion of 180 degrees. In use, the scan head 58 can be positioned at a desired angle relative to the handle to facilitate inspection of either side of a tooth (the lingual or buccal side) with minimal operator hand movement.

The probe 50 can include indexing features that retain the scan head 58 in one of multiple positions relative to the handle 56 during use. For example, the distal end portion of the handle 56 can include a plurality of spring-biased balls 70 configured to be received in a correspondingly-shaped detent or recess in the scan head 58. In this manner, as the scan head 58 is pivoted relative to the handle 56, at least one of the balls 70 is received in the detent in the scan head. The engagement of the ball 70 within the detent is sufficient to hold the scan head in place relative to the handle during a procedure yet allow manual pivoting of the scan head when so desired by the user. In alternative embodiments, the scan head 58 can include one or more balls 70 while the handle 56 can include one or more detents to permit indexing of the scan head relative to the handle.

Figure 6:
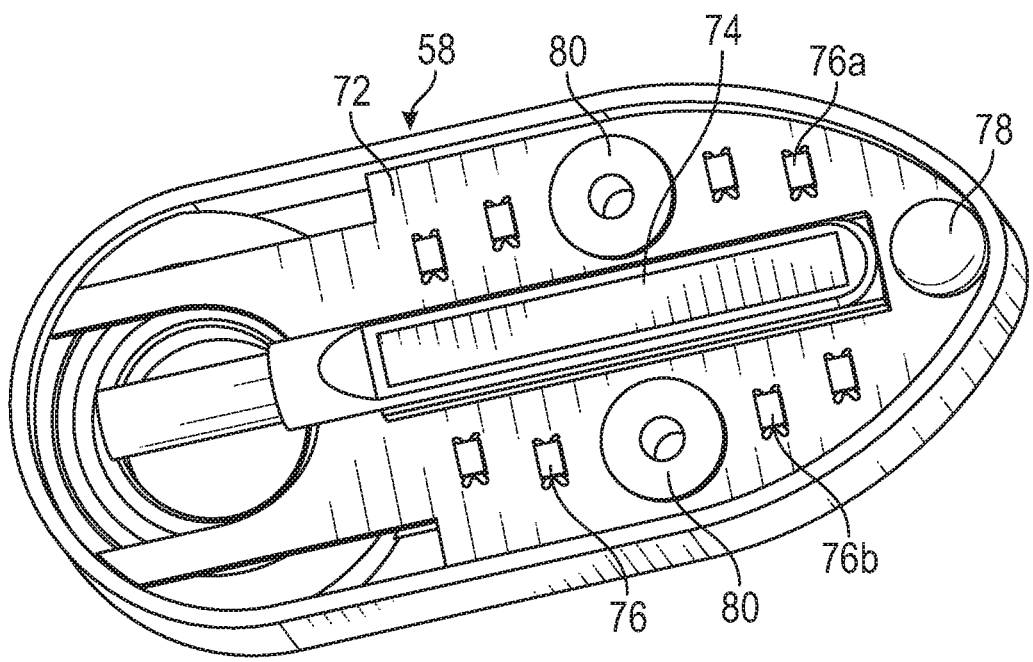
FIG. 6 is an enlarged, perspective view of the scan surface of the probe of FIG. 5.
Figure 7:
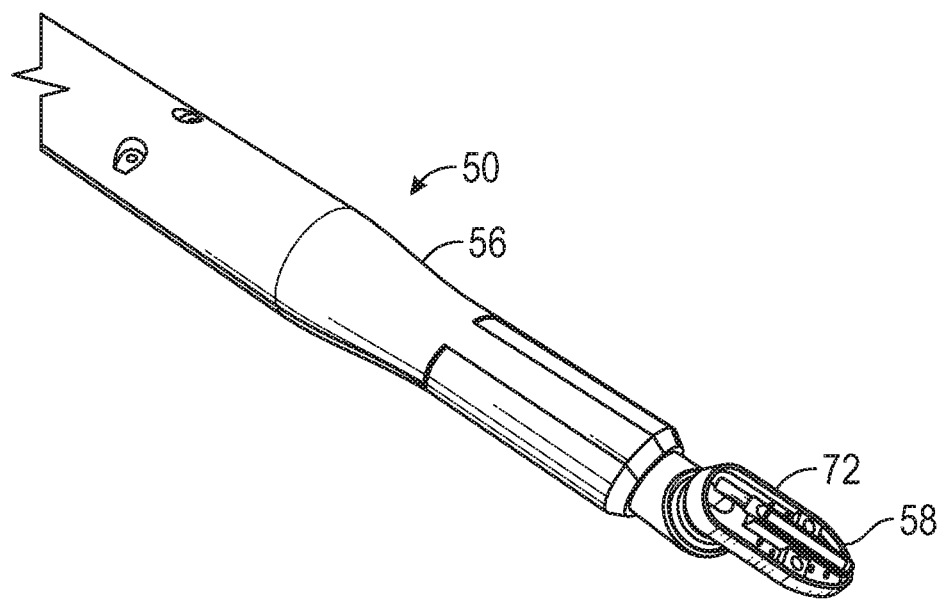
FIG. 7 is another perspective view of the probe of FIG. 5, showing the scan surface.

Referring to FIGS. 6 and 7, the scan head 58 includes a scanning surface 72 having one or more sensors for generating images of tissue inside the patient's mouth, including ultrasound images and/or optical images. As best shown in FIG. 6, the scanning surface 72 can include an ultrasonic array 74, one or more LED's 76, at least one additional LED 78, and one or more light-based, infrared or other image sensors 80. The LED 78 desirably comprises a high intensity, multi-color, infrared other optical wavelength LED. The illustrated configuration includes a total of eight LED's 76, with four LED's 76a on one side of the ultrasonic array 74 and four LED's 76b on the opposite side of the ultrasonic array 74. However, in other embodiments, a greater or fewer number of LED's may be used. Further, the illustrated configuration includes two image sensors 80, with one sensor 80 on one side of the ultrasonic array 74 and one on the opposite side of the ultrasonic array 74. However, in other embodiments, a greater or fewer number of sensors 80 can be used.

The ultrasonic array 74 can include an array of ultrasonic transducers or elements that are configured to operate as transmitters and receivers. The ultrasonic array 74 can comprise, for example, piezoelectric type ultrasonic transducers (e.g., piezoelectric micro-machined ultrasonic transducers (PMUT)), capacitive micro-machined ultrasonic transducers (CMUT), polyvinylidene fluoride transducers, or ployvinylidene difluoride (PVDF) transducers. The transducers are configured to emit and receive ultrasonic waves, such as at a frequency in a range of about 0.5 MHz to about 40 MHz, and more desirably in a range of about 7 MHz to about 35 MHz, with 10 MHz being a specific example.

In particular embodiments, the ultrasonic array 74 can be a one-dimensional array of elements, such as a 1×128 array of elements, or a 1×256 array of elements. In other embodiments, the array 74 can be a two-dimensional array, such as a 2×64 array of elements, or a 2×128 array of elements.

Figure 12:
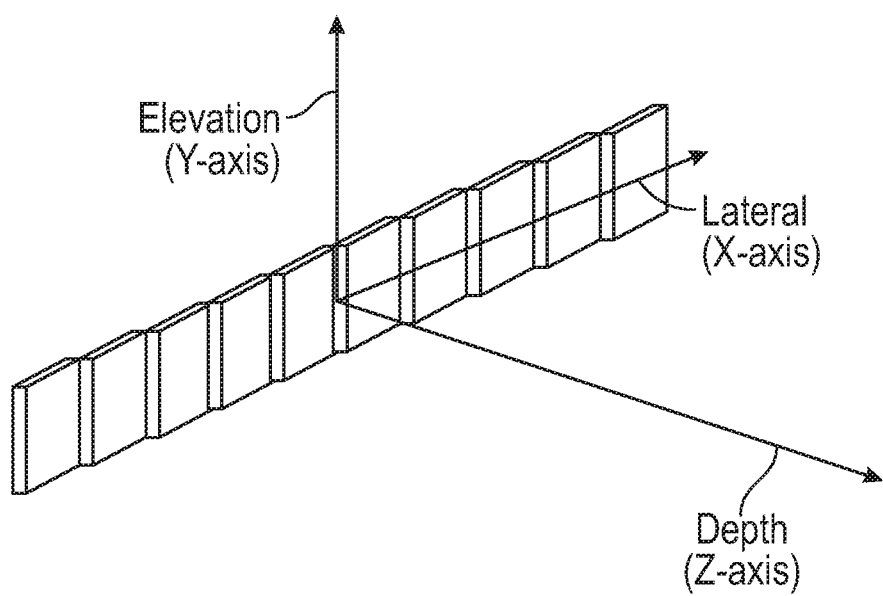
FIG. 12 is a schematic illustration of a one-dimensional transducer array that can be implemented in a scan head.

The overall physical size of the ultrasonic array 74 is minimized so that the scan head can mount the ultrasonic array along with the other components and still fit comfortably within a patient's mouth. In particular embodiments, the ultrasonic array 74 comprises a one-dimensional array having a length of 40 mm or smaller, more desirably 20 mm or smaller, with 13 mm being specific example, a width of 10 mm or smaller, with 3 mm being a specific example, and a thickness of 15 mm or smaller, with 4 mm being a specific example. FIG. 12 is a schematic illustration of a one-dimensional transducer array that can be implemented in the scan head.

In use, each of the individual ultrasonic transducers or elements of the array produce ultrasonic waves that travel through the gum tissue in the mouth and are partially reflected by structures under the gum line to produce echo returns. The transducers generate ultrasonic receive signals in response to the echo return signals. The ultrasonic receive signals are transmitted to the computing device 42 for processing and generating ultrasonic images of a tooth or teeth below the gum line that can be displayed on the display 34. In particular embodiments, the ultrasonic images include soft tissue layers of the gum, including internal tissue layers, surrounding the tooth or teeth.

Each of the ultrasonic transducers of the array can have two leads or wires that extend through the handle where they can be electrically connected to additional wiring that is connected to the computing device 42. For example, the handle can house multiple coaxial wires that carry signals from the transducers to the computing device. In certain embodiments, one or more flexible circuits extend from inside the scan head 58 into the inside of the handle 56 and electrically connect the transducers to the coaxial wires within the handle 56.

Figure 9:
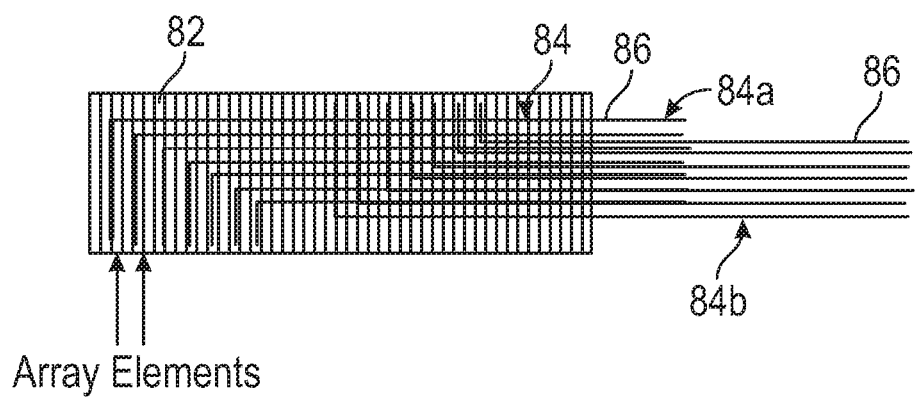
FIG. 9 is an electrical diagram of an ultrasonic transducer array and corresponding wiring connected to transducers of the array, according to one embodiment.

FIG. 9, for example, shows a schematic illustration of a transducer array 82 and a plurality of groups 84 of wires 86 extending from the array 82. Although two groups 84*a*, 84*b* are shown for purposes of illustration, one such group or more than two groups may be used. Each group 84 includes a plurality of wires 86 extending from respective transducers of a section of the array. Each group 84 can be arranged in a flexible circuit, such as by mounting a group of wires on a flexible substrate or support (e.g., a polymeric sheet). The flexible circuits can be arranged together in a stacked configuration inside the scan head 58 and the handle 56. The wires 86 within each flexible circuit can then be electrically connected to coaxial wires that are in turn connected to the computing device 42. In particular embodiments, all of the wires 86 can be mounted on a flexible substrate, which can then be folded lengthwise to form multiple fold layers of a flexible circuit.

Referring again to FIG. 6, the image sensors 80 can comprise sensors of the type used in digital cameras, such as CCD or CMOS sensors. While the ultrasonic transducers are used for generating ultrasonic images of a tooth or teeth below the gum line and surrounding tissue, the sensors 80 are used for generating optical images of the surfaces of a tooth or teeth above the gum line, as well as the exposed surfaces of the gums. In other embodiments, other types of light-based sensors can be used, such as infrared, near infrared, or ultraviolet sensors. As used herein, "optical images" refer to surface images produced by light-based sensors that reproduce an object from reflected, refracted, or diffracted light waves using a lens or mirror system. In some embodiments, the "optical images" are produced by light waves having a wavelength in the ultraviolet, visible or infrared bands (100 nm to 1 mm). In other embodiments, the "optical images" are produced by light waves having a wavelength in the visible band (400 nm to 800 nm), the infrared band (greater than 400 nm to 1 mm), or the visible and infrared band. As used herein, an "optical image" includes a visible radiation pattern of an image (in the case of visible light), an electrical or digital representation of an image, and a viewable image presented on a display.

The LED's 76 function as a light source to illuminate the surface inside the patient's mouth that is being scanned by sensors 80. Desirably, the intensity of the LED's 76 can be adjusted (e.g., with button 60*c*) as needed to decrease the reflection on tissue facing the sensors 80. The LED 78 desirably is selected to have a greater intensity than LED's 76 and can be used to detect dental caries (cavities). In alternative embodiments, the scan head can include other types of light sources, such as incandescent light bulbs, in lieu of or in addition to the LED's 76, 78.

In particular embodiments, the LED's 76 and/or 78 and the ultrasonic array 74 are pulsed together in a synchronized manner, together with the sensors 80. A short pulse duration of the LED's can reduce thermal heating of the scan head.

Alternatively, the probe 50 can include a separate pulse generator electrically connected to the LED's 76 and/or 78 to produce ultrasonic images via photo-acoustic imaging without ultrasonic transmitters. The LED's produce short optical pulse signals on the surface of tissue inside the mouth (teeth or gum tissue), which can be synchronized with the sensors 80. The short optical pulse signals on the surface of the teeth or gums generate ultrasound waves via photoacoustic effect that travel through tissue in the mouth (teeth, gums and/or bone). The ultrasound waves that are reflected from the internal structures of the tissue are received by piezoelectric transducers and converted into electrical signals, which can be processed and converted into viewable ultrasonic images. In an alternative embodiment, the LED's 76 or 78 can be replaced with one or more lasers that are electrically connected to a switch that controls pulsing or modulation of the one or more lasers to generate ultrasound waves via photo-acoustic effect.

Figure 10:
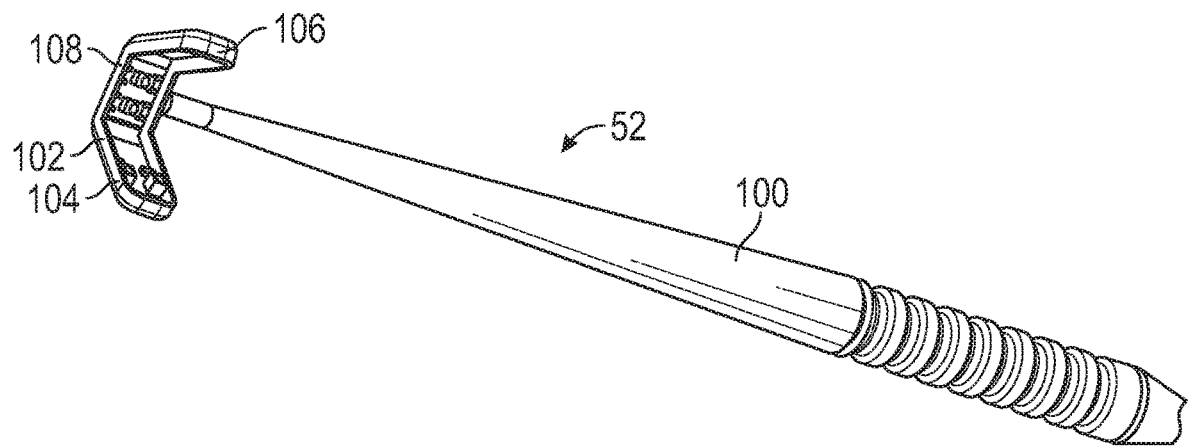
FIG. 10 is a perspective view of another intraoral probe of the dental imaging apparatus of FIGS. 2-4.
Figure 11:
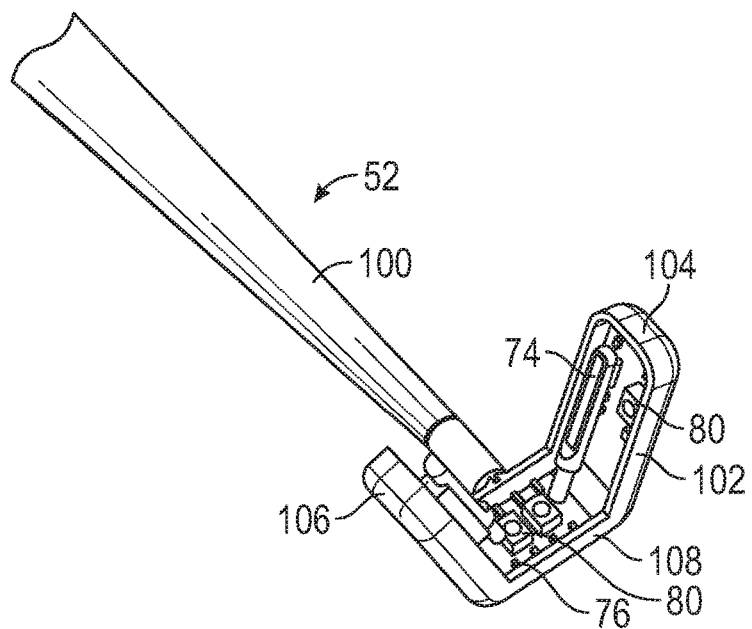
FIG. 11 is an enlarged perspective view of the scan head and the distal end portion of the handle of the probe of FIG. 10.

FIGS. 10-11 show the second probe 52 in greater detail. As shown, the second probe 52 can include a handle 100 and a scan head 102 coupled to the distal end portion of the handle 100. The scan head 102 in the illustrated embodiment includes first and second side scan panels 104 and 106, respectively, for scanning or imaging opposing sides of a tooth (the buccal and lingual surfaces) and an intermediate scan panel 108 for scanning or imaging the occlusal surface of a tooth. In some embodiments, the side scan panels 104, 106 and the intermediate scan panel 108 can be sized to extend over and scan the surfaces of multiple teeth simultaneously.

As best shown in FIG. 11, the side scan panel 104 has a scanning surface that can include one or more image sensors 80 and at least one ultrasonic array 74. Although not shown, the side scan panel 104 can also include one or more LED's 76, 78. The side scan panel 106 similarly has a scan panel that can include one or more image sensors 80, at least one ultrasonic array 74, and one or more LED's 76, 78. In particular embodiments, the layout of sensors 80, the array 74 and LED's on the scan surface of the side scan panel 106 is a mirror image of the layout of the same components of the scan surface of the side scan panel 104. The intermediate scan panel 108 has a scanning surface that includes one or more image sensors 80 (two in the illustrated embodiment) and one or more LED's 76. In the illustrated configuration, there are two rows of multiple LED's 76 (four in each row in the illustrated embodiment) on opposite sides of sensors 80.

Although not shown, in some embodiments, the intermediate scan panel 108 also can include at least one ultrasonic transducer. In FIG. 10, the side scan panels 104, 106 are shown without ultrasonic arrays 74 to illustrate an embodiment of the scan head 102 that is used to generate optical images only. In alternative embodiments, one of the side scan panels 104, 106 can include one or more ultrasonic transducers that are configured to operate as transmitters and the other side scan panel 104, 106 can include one or more ultrasonic transducers that are configured to operate as receivers that receive signals transmitted through tissue in the mouth from the transmitters.

Prior to or after each use on a patient, the operator sterilizes the probes 50, 52, such as using a cold sterilization method that can include wiping the probes with a liquid cleanser. Surfaces of the probes 50, 52, including surfaces of the handles and the scan heads, can be formed from materials that changes color upon contact with the cleaning agent to confirm the probes have been properly sterilized. The sterilization process can be recorded by the cameras of the probes and saved in memory to ensure the cleaning process has been followed and the probes are ready for use on the next patient. In some cases, the probes can be manufactured for a one-time use, in which case the probes can be disposed after use.

In use, the operator selects a probe and positions the scan head at the desired position within the mouth to be inspected. The cameras can produce real-time optical image(s) of the surfaces of tissue inside of the mouth, which can be shown on the display 34. While viewing the display, the operator can position the scan head at the exact location within the mouth requiring inspection. At the same time, ultrasound image(s) of the tooth below the gum line and surrounding tissue can also be provided in real-time. In certain embodiments, for example, the display 34 can have split-screen having a first display area for displaying the optical image(s) captured by the cameras and a second display area for displaying the ultrasound image(s), which can be the internal structure of the tissue along a plane that is perpendicular the surface of the tissue shown in the optical image(s). In other embodiments, separate displays 34 can be provided for displaying the optical image(s) captured by the cameras and for the ultrasound image(s).

Figure 13:
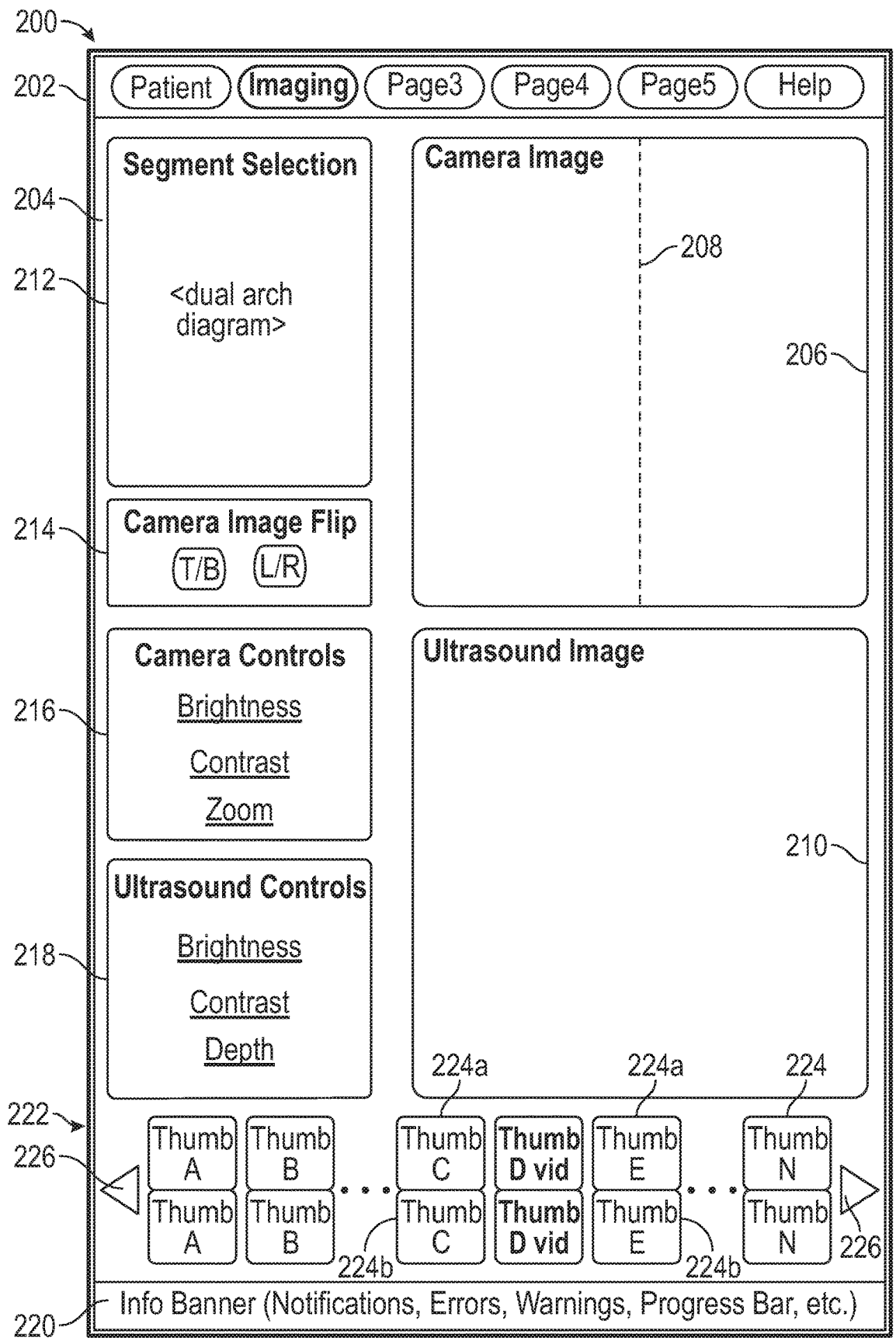
FIG. 13 shows one embodiment of a graphical user interface that includes display areas for displaying optical and ultrasound images.

FIG. 13 shows one embodiment of a graphical user interface 200 that includes display areas for displaying optical and ultrasound images. The interface 200 can include a navigation pane 202, a display page (e.g., imaging page 204), and an information banner 220.

A user can use the navigation pane 202 to navigate between display pages by clicking and/or pressing display page indicators corresponding to each display page (e.g., indicators labelled "Patient," "Imaging," and "Help" in FIG. 13). The display pages can include, for example, a patient page displaying patient information, an imaging page 204 displaying optical and ultrasound images, a help page displaying troubleshooting information and/or instructions, and/or other various pages. In some embodiments, the navigation pane 202 and/or the information banner 220 can remain visible on all display pages.

In some embodiments, depending on system state, not all display pages may be accessible to a user at any given time (e.g., some display pages may become inaccessible after they have been used). In some embodiments, a user may navigate through the display pages in a particular order (e.g., left to right) throughout the duration of a procedure and may only be able to access a particular page at a particular point in the procedure. In other embodiments, a user can use the navigation pane 202 to access any display page at any time throughout a procedure.

As shown in the illustrated embodiment, the imaging page 204 can include a first display area 206 (labeled "camera image" in FIG. 13) provided for displaying an optical image. The first display area 206 can include a dashed line 208 or other type of indicia that indicates, for example, the location of the image plane of a simultaneously acquired ultrasound image. The ultrasound image can be a simultaneously acquired orthogonal ultrasound image plane. A second display area 210 (labeled "ultrasound image" in FIG. 13) can be provided for displaying the simultaneously acquired ultrasound image. The simultaneous acquired ultrasound image can be orthogonal to the optical image shown in the first display 206. In alternative embodiments, the imaging page can include (in lieu of or in addition to display areas 206, 210), an imaging area that displays a composite or fused image that includes all or part of the optical image and all or part of the ultrasound image.

As shown, the imaging page 204 can include various buttons or controls for operating the system. The controls can include a segment selection pane 212 (labelled "Segment Selection" in FIG. 13) that allows a user to select a section of teeth (i.e., an arch segment) being imaged. The controls can further include a system orientation pane 214 (labelled "Camera Image Flip" in FIG. 13), which allows a user to manually adjust the orientation of the system. Generally, the arch segment selected using the segment selection pane 212 will automatically orient up/down and left/right directions for the display areas 206, 210, however, a user can use the system orientation pane 214 to manually override the automatic orientation if it does not match the user's desired orientation. The controls can further include a camera control pane 216 (labelled "Camera Controls" in FIG. 13) that allows a user to adjust the brightness, contrast, and zoom of the camera, and an ultrasound control pane 218 (labelled "Ultrasound Controls" in FIG. 13) that allows a user to adjust the brightness, contrast, and depth of the ultrasound.

The imaging page 204 can further include an image storage display 222. A user can save pairs of images (e.g., as single-frame snapshots and/or multiple-frame video clips) to the image storage display 222 as a pair of image thumbnails 224. Each pair of thumbnails 224 can consist of a camera image 224a and an ultrasound image 224b. Image pair storage can be controlled, for example, using buttons on the device handle 56. When a user saves a pair of images as thumbnails 224 to the image storage display 222, each thumbnail 224 is given a unique identifier (e.g., an ID number, name, and/or color, etc.). A user can navigate through the list of image thumbnails 224 by scrolling using left and right scroll arrows 226.

A user can review stored images by selecting a pair of thumbnails 224 from the storage display 222. This interrupts the real-time images shown in the first and second display areas 206, 210 and instead displays the stored images. A user can return to a real-time image by clicking within the first and/or second display area 206, 210. If a user selects a video clip thumbnail, all stored frames of the video clip can be displayed individually in the storage display 222, from first frame to last frame. A user can use the scroll arrows 226 to navigate through the frames of the video clip. To return to live imaging and restore the storage display 222, a user can click within the first and/or second display area 206, 210. Stored images can be used to evaluate changes to a specific tooth or teeth and surrounding tissue over time.

As stated above, the graphical user interface 200 can also include an information banner 220. The information banner 220 can display, for example, notifications, errors, warnings, and/or progress bars for the procedure or portions of the procedure.

The buttons and controls of the graphical user interface 200 can be controlled, for example, with a computer mouse or a touch screen. In some embodiments, the graphical user interface 200 can be, for example, between 20-30 cm wide, preferably 24 cm wide, and between 35-55 cm long, preferably 42 cm long.

As noted above, the ultrasound images can be used detect, for example, cracks in teeth below the gum line or gum disease in the perio pockets that are not visible using cameras or other light-based scanners. Video and/or still images generated by the cameras and the ultrasonic transducers can be saved in the computing device for further processing. For example, in one application, a composite image of an entire tooth or teeth and surrounding tissue can be generated by combining an optical image and an ultrasound image. Conventional image fusion techniques can be used to generate a composite or fused image that includes all or part of the optical image and all or part of the ultrasound image. Additionally, the images can be used for making dental restorations or implants. For example, as noted above, the images can be entered into a Computer Aided Design (CAD) software program that is used to create drawings or images of dental restorations or implants designed for a particular patient.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the inspection site. As used herein, the term "distal" refers to a position, direction, or portion of a device that is further away from the user and closer to the inspection site. The terms "longitudinal" and "axial" refer to an axis extending in the proximal and distal directions, unless otherwise expressly defined.

Any of the disclosed methods involving software, such as the methods for processing signals from an intraoral device and generating viewable images, can be implemented as computer-executable instructions or a computer program product stored on one or more computer-readable storage media and executed on a computing device (e.g., any available computing device, including smart phones or other mobile devices that include computing hardware). Tangible computer-readable storage media are any available tangible media that can be accessed within a computing environment (e.g., one or more optical media discs such as DVD or CD, volatile memory components (such as DRAM or SRAM), or nonvolatile memory components (such as flash memory or hard drives)). The term computer-readable storage media does not include signals and carrier waves. In addition, the term computer-readable storage media does not include communication connections.

Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network, or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, JavaScript, Python, Ruby, ABAP, SQL, Adobe Flash, or any other suitable programming language, or, in some examples, markup languages such as html or XML, or combinations of suitable programming languages and markup languages. Likewise, the disclosed technology is not limited to any particular computer or type of hardware. Certain details of suitable computers and hardware are well known and need not be set forth in detail in this disclosure.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. An intraoral scanning device comprising:
 a scan head sized and shaped to be placed inside a patient's mouth, the scan head comprising at least one ultrasonic transducer for generating ultrasonic images and at least one light-based image sensor for generating optical images.

2. The intraoral scanning device of claim 1, wherein the at least one ultrasonic transducer comprises an array of ultrasonic transducers.

3. The intraoral scanning device of claim 1, wherein the scan head comprises at least one light source.

4. The intraoral scanning device of claim 3, wherein the at least one light source comprises an LED.

5. The intraoral scanning device of claim 1, wherein the at least one light-based image sensor comprises a CCD or CMOS sensor.

6. The intraoral scanning device of claim 1, wherein the at least one ultrasonic transducer comprises an array of ultrasonic transducers and the at least one light-based image sensor comprises first and second light-based image sensors positioned on opposite sides of the array of ultrasonic transducers.

7. The intraoral scanning device of claim 1, further comprising a handle, and the scan head is coupled to one end of the handle.

8. The intraoral scanning device of claim 7, wherein the scan head is configured to be pivotable relative to the handle.

9. The intraoral scanning device of claim 1, wherein the scan head comprises first and second opposing scan surfaces configured to be placed against or adjacent opposing sides of a tooth.

10. The intraoral scanning device of claim 9, wherein the scan head comprises a third scan surface extending between the first and second scan surfaces, the third scan surface configured to be placed against or adjacent an occlusal surface of a tooth.

11. An intraoral scanning device comprising:
 a handle; and
 a scan head coupled to a distal end portion of the handle and sized and shaped to be placed inside a patient's mouth, the scan head comprising at least one sensor for generating images of tissue inside the patient's mouth, wherein the scan head is configured to be pivotable relative to the handle about a pivot axis.

12. The intraoral scanning device of claim 11, wherein at least one of the handle and the scan head comprises an indexing feature configured to retain the scan head relative to the handle in one of a plurality of different positions relative to the handle.

13. The intraoral scanning device of claim 12, wherein the indexing feature comprises a plurality of balls on one of the handle and the scan head and the other of the handle and the scan head comprises at least one detent configured to receive one of the balls as the scan head is pivoted relative to the handle.

14. The intraoral scanning device of claim 11, wherein the scan head comprises at least one ultrasonic transducer.

15. The intraoral scanning device of claim 11, wherein the scan head comprises at least one light-based image sensor.

16. A dental imaging apparatus comprising:
 an intraoral device comprising at least one ultrasonic transducer for generating ultrasonic images and at least one light-based image sensor for generating optical images; and
 a visual display in communication with the intraoral device, the visual display configured to display ultrasonic images and optical images.

17. The dental imaging apparatus of claim 16, wherein the intraoral device comprises a handle and a scan head coupled to one end of the handle, wherein the sensors are mounted on the scan head.

18. A method comprising:
 inserting an intraoral device inside a patient's mouth, the intraoral device comprising at least one ultrasonic transducer and at least one light-based image sensor; and
 generating an ultrasound image and an optical image of tissue inside the patient's mouth.

19. The method of claim 18, further comprising displaying the ultrasound image and the optical image on a visual display.

20. The method of claim 19, wherein the act of displaying comprises simultaneously displaying the ultrasound image and the optical image on the visual display.

21. The method of claim 20, wherein the optical image is an image of a portion of a tooth or teeth above the gum line and the ultrasound image is an image of a portion of the tooth or teeth below the gum line and tissue surrounding the tooth or teeth.

22. The method of claim 21, further comprising using the optical image as a guide to evaluate gum tissue of the tooth or teeth.

23. The method of claim 21, further comprising storing the optical image and the ultrasound image and evaluating changes to the tooth or teeth and surrounding tissue over time.

24. The method of claim 18, further comprising positioning the intraoral device at a particular location inside the patient's mouth while viewing the optical image on a display.

25. The method of claim 18, wherein the act of generating comprises generating a three-dimensional volumetric optical image of a tooth or teeth above the gum line and generating a three-dimensional ultrasonic image of a portion of the tooth or teeth below the gum line and tissue surrounding the tooth or teeth.

26. The method of claim 25, further comprising generating a fused image comprising the three-dimensional volumetric optical image and the three-dimensional ultrasonic image.

27. A dental imaging apparatus comprising:
 an intraoral device comprising at least three scan panels configured to be placed adjacent three surfaces of a tooth or teeth, each scan panel having at least one ultrasonic transducer for generating ultrasonic images and at least one light-based sensor for generating an optical images; and a computing device in communication with the intraoral device configured to generate a three-dimensional impression of intraoral structure in multiple directions simultaneously.

* * * * *